United States Patent [19]

Luteri

[11] 4,284,425

[45] Aug. 18, 1981

[54] METHOD OF INCREASING THE RECOVERABLE SUGAR FROM SUGAR BEETS

[75] Inventor: George F. Luteri, Mt. Prospect, Ill.

[73] Assignee: Velsicol Chemical Corporation, Chicago, Ill.

[21] Appl. No.: 159,405

[22] Filed: Jun. 13, 1980

[51] Int. Cl.³ ............................................. A01N 37/00
[52] U.S. Cl. ............................................ 71/27; 71/88; 71/107; 127/42
[58] Field of Search ................... 71/1, 11, 26, 27, 88, 71/107; 127/42

[56] References Cited

U.S. PATENT DOCUMENTS

| | | | |
|---|---|---|---|
| 3,619,169 | 11/1971 | Zick | 71/107 |
| 3,767,377 | 10/1973 | Poulos | 71/107 |
| 3,862,121 | 1/1975 | Jaques et al. | 536/115 X |
| 4,042,538 | 8/1977 | Lucas | 536/115 X |

FOREIGN PATENT DOCUMENTS 2251264  6/1975  France ....................................... 127/42

Primary Examiner—Ferris H. Lander
Attorney, Agent, or Firm—Dietmar H. Olesch; Robert J. Schwarz

[57] ABSTRACT

This invention discloses a method of increasing the yield of sugar obtained from sugar beets by treating the beet plants with sucrose tri(2-methoxy-3,6-dichlorobenzoate).

3 Claims, No Drawings

METHOD OF INCREASING THE RECOVERABLE SUGAR FROM SUGAR BEETS

This invention relates to a method of increasing the yield of sugar obtained from sugar beets. More particularly, this invention relates to a method of increasing the recoverable sugar in sugar beets by treating the sugar beet plants during their growing or maturing season with a sucrose ester of dicamba.

Surprisingly, it has now been found that the recovery of sugar from sugar beets can be substantially increased through the use of sucrose tri(2-methoxy-3,6-dichlorobenzoate) represented by the following structural formula:

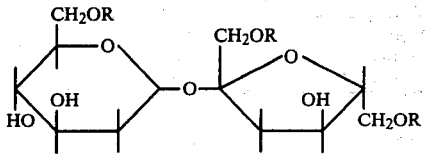

wherein each R is

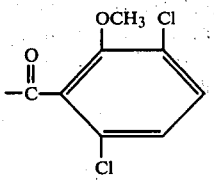

Accordingly, one embodiment of the present invention resides in a method of increasing the recoverable sugar in sugar beets which comprises contacting the growing sugar beet plant with an effective amount of sucrose tri(2-methoxy-3,6-dichlorobenzoate) at least two weeks before harvest.

The effective compound of the present invention can be prepared by the procedure detailed in the following example.

EXAMPLE 1

Preparation of Sucrose Tri(2-methoxy-3,6-dichlorobenzoate)

Sucrose (34.2 grams; 0.1 mole) and pyridine (300 ml) were charged into a glass reaction vessel equipped with a mechanical stirrer, thermometer and addition funnel. The mixture was stirred and 2-methoxy-3,6-dichlorobenzoyl chloride (71.5 grams, 0.3 mole) was added dropwise over a period of 8 hours. After this time the mixture was stripped of pyridine under reduced pressure and the residue was dissolved in ethyl acetate (500 ml). The ethyl acetate solution was then washed with dilute hydrochloric acid, with dilute sodium carbonate, with aqueous sodium chloride (5% concentration) and with water. The washed solution was dried over anhydrous magnesium sulfate and then stripped of solvent to yield the desired product sucrose tri(2-methoxy-3,6-dichlorobenzoate) as a glass.

To effect the method of this invention, sugar beet plants are treated at a relatively late stage of development with an effective amount of sucrose tri(2-methoxy-3,6-dichlorobenzoate). This treatment is preferably carried out during that stage of development of the sugar beet plant wherein sugar formation takes place. Thus, under normal growing conditions and common cultivation practice, the active compound can be applied to the sugar beet plants during the period of from about 2 to about 10 weeks before harvesting and preferably during the period of from about 3 to about 8 weeks before harvesting.

The amount of the sucrose tri(2-methoxy-3,6-dichlorobenzoate) required to effectively increase the recoverable sugar from sugar beets can vary somewhat depending upon such factors as the time of application, the weather, crop density and the like. Generally, an amount ranging from about 0.1 ounce to about 4 pounds per acre and preferably from about 0.1 ounce to about 2 pounds per acre can be used. While amounts greater than those mentioned can be used, they will not result in an advantage that would warrant the expense and are therefore not practical.

For practical use in treating sugar beets, the compound of this invention generally is incorporated into compositions or formulations which comprise an inert carrier and an effective amount of the compound. These compositions enable the active compound to be conveniently applied to the sugar beets in any desired quantity. These formulations can be liquids such as solutions, aerosols or emulsifiable concentrates or they can be solids such as dusts, granules or wettable powders.

The preferred compositions are liquid formulations, particularly emulsifiable concentrates. Emulsifiable concentrates comprise the active compound according to this invention and as the inert carrier, a solvent and an emulsifier. Such emulsifiable concontrates can be extended with water and/or oil to any desired concentration of the active compound for application as sprays to the sugar beets. The emulsifiers most commonly used in these concentrates are nonionic or mixtures of nonionic with anionic surface-active agents. With the use of some emulsifier systems an inverted emulsion (water-in-oil) can be prepared.

Solid formulations such as dusts, for example, can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

Typical formulations according to the present invention useful for increasing the recoverable sugar in sugar beets are illustrated in the following examples wherein the quantities are in parts by weight.

EXAMPLE 2

Preparation of an Emulsifiable Concentrates

The following ingredients are blended thoroughly until a homogeneous liquid concentrate is obtained. This concentrate is mixed with water to give an aqueous dispersion containing the desired concentration of the active ingredients for use as a spray.

| | |
|---|---|
| Sucrose tri(2-methoxy-3,6-dichlorobenzoate) | 25 |
| Sodium lauryl sulfate | 2 |
| Sodium lignin sulfate | 3 |
| Aromatic hydrocarbon solvent | 70 |

EXAMPLE 3

Preparation of a Wettable Powder

The following components are mixed intimately in conventional mixing or blending equipment and are then ground to a powder having an average particle size of less than about 50 microns. The finished powder is dispersed in water to give the desired concentration of active compound.

| | |
|---|---|
| Sucrose tri(2-methoxy-3,6-dichlorobenzoate) | 50 |
| Fuller's earth | 47 |
| Sodium lauryl sulfate | 2.5 |
| Methyl cellulose | 0.5 |

EXAMPLE 4

Preparation of a Dust

The following ingredients are mixed thoroughly and are then ground to an average particle size of less than about 50 microns to give a dust suitable for application with conventional dusting equipment.

| | |
|---|---|
| Sucrose tri(2-methoxy-3,6-dichlorobenzoate) | 10 |
| Powdered talc | 90 |

The effectiveness of the compound sucrose tri(2-methoxy-3,6-dichlorobenzoate) for increasing the recoverable sugar in sugar beets was demonstrated in a field experiment wherein diploid monogerm hybrid sugar beets were planted April 18 and thinned to one plant one foot apart with 22-inch row spacing. On September 4, 25 foot by 6 row plots were each sprayed at a rate of 0.5 and 2.0 ounces of sucrose tri(2-methoxy-3,6-dichlorobenzoate) respectively. The plots were surface irrigated at 2-week intervals to maintain normal growth. The crop was harvested on October 15 and the recoverable sugar was determined and measured on a percent basis in comparison to concentrated controls. The results of this experiment are shown in the following tables:

TABLE 1

| | Actual Values | | |
|---|---|---|---|
| | Treatment Rate | | |
| | 0.5 | 2.0 | 0 (Control) |
| Recoverable Sugar Lb/Acre | 5077.9 | 5336.1 | 4991.7 |
| Weight of Beets Tons/Acres | 22.3 | 23.3 | 21.7 |
| Percent Sugar | 14.9 | 14.8 | 14.8 |
| Percent Purity | 88.4 | 88.8 | 88.9 |
| Number of Beets/Plat | 71.4 | 70.8 | 69.6 |

TABLE II

| | Percent of Control | | |
|---|---|---|---|
| | Treatment Rate | | |
| | 0.5 | 2.0 | 0 (Control) |
| Recoverable Sugar Lb/Acre | 101.7 | 106.9 | 100 |
| Weight of Beets Tons/Acre | 102.8 | 107.3 | 100 |
| Percent Sugar | 100.1 | 99.9 | 100 |
| Percent Purity | 99.5 | 99.9 | 100 |
| Number of Beets/Plat | 102.6 | 101.7 | 100 |

I claim:

1. A method for increasing the recoverable sugar from sugar beets which comprises contacting the sugar beet plants with from about 0.1 ounce to about 4 lbs. per acre of sucrose tri(2-methoxy-3,6-dichlorobenzoate) having the formula

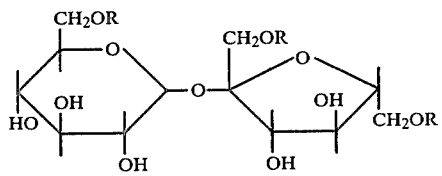

wherein each R is

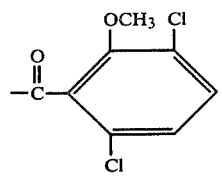

2. The method of claim 1 wherein the sugar beet plants are contacted with sucrose tri(2-methoxy-3,6-dichlorobenzoate) during the period of from about 2 to about 10 weeks before harvest.

3. The method of claim 1 wherein the sugar beet plants are contacted with about 0.1 ounce to about 4 lbs. per acre of sucrose tri(2-methoxy-3,6-dichlorobenzoate) during the period of from about 2 to about 10 weeks before harvest.

* * * * *